United States Patent
Bonda et al.

[11] Patent Number: 6,113,931
[45] Date of Patent: Sep. 5, 2000

[54] CLEAR FORMULATIONS CONTAINING DIESTERS OR POLYESTERS OF NAPHTHALENE DICARBOXYLIC ACID

[75] Inventors: Craig A. Bonda, Wheaton; Peter J. Marinelli, Bartlett; Yin Z. Hessefort, Naperville; Jagdish Trivedi, Woodridge; Gary Wentworth, Chicago, all of Ill.

[73] Assignee: The C.P. Hall Company, Chicago, Ill.

[21] Appl. No.: 09/451,974

[22] Filed: Nov. 30, 1999

Related U.S. Application Data

[63] Continuation-in-part of application No. 09/276,051, Mar. 25, 1999, Pat. No. 5,993,789.

[51] Int. Cl.[7] .............................. A61K 7/00; A61K 7/32; A61K 7/42
[52] U.S. Cl. .............................. 424/401; 424/59; 424/60; 424/65; 424/400
[58] Field of Search .................................. 424/59, 60, 65, 424/400, 401

[56] References Cited

U.S. PATENT DOCUMENTS

| | | | |
|---|---|---|---|
| 2,607,658 | 8/1952 | Govett et al. | 28/14 |
| 2,645,616 | 7/1953 | Govett et al. | |
| 2,876,163 | 3/1959 | Garizio et al. | 167/90 |
| 3,255,082 | 6/1966 | Barton | 167/90 |
| 3,740,421 | 6/1973 | Schmolka | 424/65 |
| 4,268,499 | 5/1981 | Keil | 424/68 |
| 4,278,655 | 7/1981 | Elmi | 424/47 |
| 4,308,328 | 12/1981 | Salyer et al. | 430/17 |
| 4,350,605 | 9/1982 | Hughett | 424/47 |
| 4,383,988 | 5/1983 | Teng et al. | 424/68 |
| 4,387,089 | 6/1983 | De Polo | 424/59 |
| 4,489,057 | 12/1984 | Welters et al. | 424/47 |
| 4,562,067 | 12/1985 | Hopp et al. | 424/59 |
| 4,673,570 | 6/1987 | Soldati | 424/66 |
| 4,725,430 | 2/1988 | Schamper et al. | 424/66 |
| 4,822,602 | 4/1989 | Sabatelli | 424/65 |
| 5,385,729 | 1/1995 | Prencipe et al. | 424/70.11 |
| 5,635,166 | 6/1997 | Galleguillos et al. | 424/66 |
| 5,670,140 | 9/1997 | Deflandre et al. | 424/59 |
| 5,783,173 | 7/1998 | Bonda et al. | 424/59 |
| 5,788,954 | 8/1998 | Bonda et al. | 424/59 |
| 5,849,273 | 12/1998 | Bonda et al. | 424/59 |
| 5,882,634 | 3/1999 | Allard et al. | 424/59 |
| 5,976,513 | 11/1999 | Robinson | 424/59 |

OTHER PUBLICATIONS

"Photostable Cosmetic Light Screening Composition", Author: Anon. Organization, UK Publication Source, Research Disclosure (1999), 418(Feb.), P175 (No. 41803).

Identifier—CODEN RSDSBB ISSN 0374–4363 Publisher Kenneth Mason Publications Ltd. Patent Information.

"Polyester And Copolyester Sheeting, Film And Structured Products Stabilized Against Degradation By Sunlight Or Other UV Light Sources", Author: Anon. Organization, Research Disclosure (1994), (Nov.), P601 (No. 36708).

Fox, Charles, Fox Associates, Fair Lawn, New Jersey, "Gels and Sticks Review and Update", *Cosmetics & Toiletries*, vol. 99, Nov. 1984 (pp. 19,20,22,24,25,28–30,32,34,36,38,40, 42,44,47,48,50,52,54).

Fox, Charles, Charles Fox Associates Inc., Fair Lawn New Jersey, "Antiperspirants & Deodorants Review and Update" *Cosmetics & Toiletries*, vol. 100, Dec. 1985 (pp. 27–33, 35–36, 40–41).

"Deodorant & Antiperspirant Formulary", *Cosmetics & Toiletries*, vol. 100, Dec. 1985 (pp. 65–75).

Goldembert, et al., "Silicones In Clear Formulations", D&CI, Feb. 1986, (pp. 34,38,40,44).

STN, File Supplier, Karlsruhe, DE, File Chemical Abstracts, vol. 130, AN=158258 see the abstract XP002126186 & Research Disclosure, No. 418003, Feb. 10, 1999 (1999–02–10), p. 175 UK the whole document.

*Primary Examiner*—Shelley A. Dodson
*Attorney, Agent, or Firm*—Marshall, O'Toole, Gerstein, Murray & Borun

[57] ABSTRACT

A cosmetic formulation, particularly a transparent cosmetic formulation, containing a diester or polyester of a naphthalene dicarboxylic acid having formula (I), (II), or (III), or mixtures:

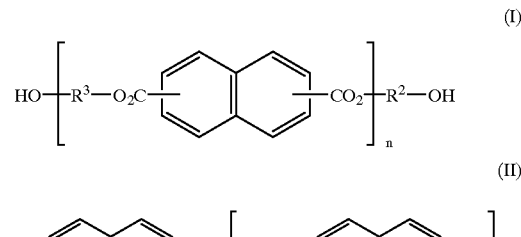

wherein each $R^1$, same or different, is an alkyl group having 1 to 22 carbon atoms, a diol having the structure HO—$R^2$—OH, or a polyglycol having the structure HO—$R^3$—(—O—$R^2$—)$_m$—OH, wherein $R^2$ and $R^3$, same or different, are each an alkylene group, straight chain or branched, having 1 to 6 carbon atoms, and wherein m and n are each 1 to about 100, or a mixture thereof.

17 Claims, No Drawings

CLEAR FORMULATIONS CONTAINING DIESTERS OR POLYESTERS OF NAPHTHALENE DICARBOXYLIC ACID

CROSS REFERENCE TO RELATED APPLICATION

This application is a continuation-in-part of application Ser. No. 09/276,051 filed Mar. 25, 1999 now U.S. Pat. No. 5,993,789.

FIELD OF THE INVENTION

The present invention is directed to clear or transparent cosmetic formulations, and methods of manufacture. In the preferred embodiment, the formulations include both an oil phase and a water phase emulsified together to form an oil in water emulsion or water in oil emulsion. More particularly, the present invention is directed to clear or transparent cosmetic formulations that include a diester or polyester of naphthalene dicarboxylic acid that is added during the manufacture of a cosmetic formulation to increase the refractive index of the oil phase to more closely equal the refractive index of the water phase such that when the two phases are mixed and emulsified, the formulation will be clear or transparent. In addition to increasing the refractive index of the compositions, the diester or polyester of naphthalene dicarboxylic acid will increase the emolliency and sunscreen protection factor (SPF) of the cosmetic formulation.

BACKGROUND OF THE INVENTION AND PRIOR ART

Clear or transparent cosmetic formulations are particularly desirable because the consumer likens transparency to purity, and because transparent formulations have esthetic appeal. Clear cosmetic formulations sometimes have been difficult to maintain stable and clear, but have been developed in each of the following areas: clear roll-ons and gels for antiperspirants; clear gel curl activators (hair moisturizers with relatively high levels of polyols); clear cosmetic sticks, including deodorant sticks, and clear antiperspirants sticks; clear solutions; clear suntan oils; clear transdermal drug administration solutions, e.g., clear benzocaine solutions; clear aftershave compositions; transparent gel toothpastes; and clear lipsticks. In accordance with the principles of the present invention, particular diesters and polyesters of naphthalene dicarboxylic acids can be included in all of the above-mentioned cosmetic formulations to increase the refractive index, thereby providing clear formulations, whether in the form of emulsions or anhydrous compositions, while providing sunscreen protection to the area of the body coated with the cosmetic formulation.

SUMMARY OF THE INVENTION

In brief, the present invention is directed to cosmetic formulations that include one or more emollients and/or skin conditioners, such as a silicone fluid, wherein the cosmetic compositions are useful as antiperspirants, deodorants, emollients, moisturizers, suntan oils, after-shave compositions, transdermal drug compositions, and the like. In the preferred embodiment, the cosmetic formulations comprise an emulsion of an oil phase and a water phase, wherein the water phase includes an emollient, humectant or other organic compound that increases the refractive index of the water phase, and the oil phase includes a sufficient amount of particular diesters or polyesters of naphthalene dicarboxylic acids to provide the oil phase and the water phase of the cosmetic formulations with approximately the same refractive index, so that the cosmetic formulations are transparent, or clear, as perceived by human eye. In other embodiments, the clear cosmetic formulations may be anhydrous, or include only an oil phase, with thickening agents such as one or more clays, e.g., hectorite or laponite, so that no emulsifying agents are required, but the composition includes one or more of the particular diesters or polyesters of a naphthalene dicarboxylic acid for emolliency and clarity.

The diesters and polyesters of a naphthalene dicarboxylic acid of the present invention have a high refractive index of at least about 1.5, preferably about 1.53, and are added to the oil phase of a oil and water emulsion to provide transparency and emolliency to the emulsion, particularly for cosmetic formulations. The esters and polyesters are reaction products of (a) a naphthalene dicarboxylic acid having the structure:

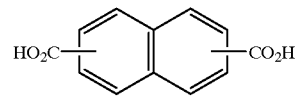

and (b) an alcohol having the structure $R^1$—OH, or a diol having the structure HO—$R^2$—OH, or a polyglycol having the structure HO—$R^3$—(—O—$R^2$—)$_m$—OH, wherein $R^1$ is an alkyl group, straight chain or branched, having 1 to 22 carbon atoms, $R^2$ and $R^3$, same or different, are each an alkylene group, having 1 to 6 carbon atoms, and wherein m and n are each 1 to about 100, preferably 1 to about 10, more preferably 2 to about 7, or a mixture thereof.

A diester of the present invention has the structure:

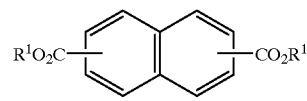

, wherein $R^1$ is as defined above.

The diesters and polyesters of naphthalene dicarboxylic acids have the general formula (I):

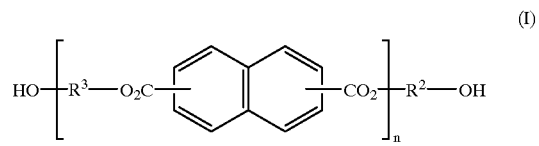

(I)

, wherein $R^2$ and $R^3$, same or different, are each an alkylene group having 1 to 6 carbon atoms, and n=1 to about 100, preferably 1 to about 10, more preferably 2 to about 7.

Alternatively, the diesters and polyesters of the present invention can be end-capped with an alcohol or an acid. The end-capped polyesters have the structural formula (II):

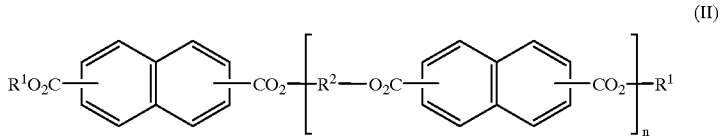

, wherein $R^1$ and $R^2$ and n are as defined above, with reference to formula (I). The two $R^1$s in formula (II) may be the same or different.

The preferred diesters and polyesters of the present invention have a weight average molecular weight of about 244 to about 4000, and more preferably about 450 to about 1500. To achieve the full advantage of the present invention, the diester or polyester has a weight average molecular weight of about 500 to about 1000.

The naphthalene dicarboxylic acid is selected from the group consisting of 1,2-naphthalene dicarboxylic acid; 1,3-naphthalene dicarboxylic acid; 1,4-naphthalene dicarboxylic acid; 1,5-naphthalene dicarboxylic acid; 1,6-naphthalene dicarboxylic acid; 1,7-naphthalene dicarboxylic acid; 1,8-naphthalene dicarboxylic acid; 2,3-naphthalene dicarboxylic acid; 2,6-naphthalene dicarboxylic acid; 2,7-naphthalene dicarboxylic acid, and mixtures thereof. Preferred dicarboxylic acids are the 2,6-, 1,5- and 1,8-naphthalene dicarboxylic acids.

The alcohol $R^1$—OH can be, for example, methanol, ethanol, propanol, isopropyl alcohol, n-butanol, sec-butanol, isobutyl alcohol, tert-butyl alcohol, amyl alcohol, 1-hexanol, 1-octanol, 1-decanol, isodecyl alcohol, 1-undecanol, 1-dodecanol, 1-tridecyl alcohol, 1-tetradecanol, 1-hexadecanol, 1-octadecanol, 1-eicosonol, 1-decosonol, 2-ethylhexyl alcohol, 2-butyloctanol, 2-butyldecanol, 2-hexyldecanol, 2-octyldecanol, 2-hexyldodecanol, 2-octyldodecanol, 2-decyltetradecanol, and mixtures thereof.

The glycol or polyglycol can be, for example, ethylene glycol, propylene glycol, 1,2-propanediol, diethylene glycol, triethylene glycol, tetraethylene glycol, dipropylene glycol, tripropylene glycol, methyl propanediol, 1,6-hexanediol, 1,3-butanediol, 1,4-butanediol, PEG-4 through PEG-100, PPG-9 through PPG-34, pentylene glycol, neopentyl glycol, trimethylpropanediol, 1,4-cyclohexanedimethanol, 2,2-dimethyl-1,3-propanediol, 2,2,4,4-tetramethyl-1,3-cyclobutanediol, and mixtures thereof.

Surprisingly, it has been found that these diesters and polyesters of naphthalene dicarboxylic acids are quite effective in formulating clear or transparent cosmetic formulations, having increased emolliency, and in providing UV sunlight protection to skin.

Accordingly, one aspect of the present invention is to provide a stable sunscreen composition that includes a diester or polyester of one or more naphthalene dicarboxylic acids as a means for raising the refractive index and increasing the emolliency of a cosmetic formulation, said naphthalene dicarboxylic acid diester/polyester having formula (I) or (II), also being capable of stabilizing a dibenzoylmethane derivative UV-A filter, particularly PARSOL® 1789, if sunscreen protection is a goal, e.g., in a lipstick formulation.

Another aspect of the present invention is to provide an improved, stable sunscreen composition containing a diester and/or polyester of a naphthalene dicarboxylic acid that increases the effectiveness of dibenzoylmethane derivative sunscreen compounds, particularly 4-(1,1-dimethylethyl)-4'-methoxydibenzoylmethane (PARSOL® 1789), in SPF and in duration.

The above and other aspects and advantages of the present invention will become more apparent from the following detailed description of the preferred embodiments.

DETAILED DESCRIPTION OF THE PREFERRED EMBODIMENTS

The clear cosmetic formulations of the present invention include about 1% to about 20%, preferably about 1% to about 10% by weight of a diester and/or polyester of one or more naphthalene dicarboxylic acid, having formula (I) or (II).

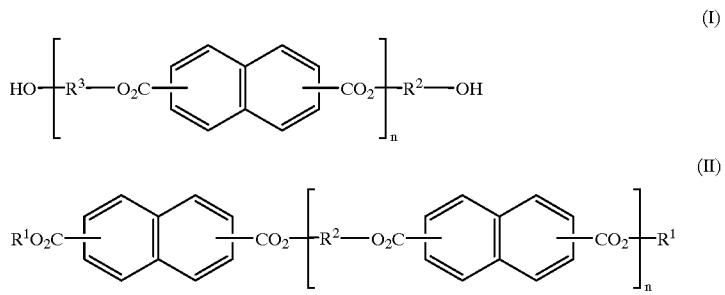

wherein each $R^1$, same or different, is an alkyl group having 1 to 22 carbon atoms, or a diol having the structure HO—$R^2$—OH, or a polyglycol having the structure HO—$R^3$—(—O—$R^2$—)$_m$—OH, and, wherein $R^2$ and $R^3$, same or different, are each an alkylene group, straight chain or branched, having 1 to 6 carbon atoms, wherein m and n are each 1 to about 100, preferably 1 to about 10, more preferably 2 to about 7, or a mixture thereof.

Typical formulations that should be transparent are as follows, having sufficient diester and/or polyester of a naphthalene dicarboxylic acid to provide transparency and/or increased emolliency. In formulations that include emulsified oil and water phases, one or more of a diester and/or polyester of a naphthalene dicarboxylic acid are added to the oil phase in an amount sufficient such that the oil and water phases have an index of refraction within about 0.1, preferably within about 0.05, more preferably within about 0.01. In some cases, it is necessary to add a water-soluble organic or inorganic material, e.g., propylene glycol, to the water phase to raise the refractive index of the water phase to match the refractive index of the oil phase.

A different approach to clear gel antiperspirants is the following:

CLEAR FIRM ANTIPERSPIRANT GEL

|  | Function | % |
|---|---|---|
| Oil Phase A: | | |
| Procetyl 10 (Croda PPG 10 Cetyl Ether) | emollient, skin conditioning agent | 4.0 |
| Dow Corning 344 Fluid (Cyclomethicone) | emollient, skin conditioning agent | 20.0 |
| Procetyl AWS (Croda PPG 5-Ceteth 20) | surfactant | 16.0 |
| Diethylhexyl naphthalate | emollient, refractive index increasing agent | 14.0 |
| Water Phase B: | | |
| Aluminum Chlorhydrate, 50% Aq | active antiperspirant compound | 46.0 |

Slight modification of the above system can convert it to use as a vehicle for "actives" other than aluminum antiperspirant salts. One such base is this (water-in-silicone) microemulsion with excellent esthetic properties:

|  | Function | % |
|---|---|---|
| EMOLLIENT MICROEMULSION | | |
| Oil Phase A: | | |
| Procetyl AWS (Croda PPG 5-Ceteareth 20) | surfactant | 25 |
| Procetyl 10 (Croda PPG 10-Cetyl Ether) | emollient, skin conditioning agent | 5 |
| Diethylhexyl naphthalate | emollient, refractive index increasing agent | 14 |
| Dow Corning 344 Fluid (cyclomethicone) | emollient, skin conditioning agent | 25 |
| Water Phase B: | | |
| Water | | 31 |
| ANHYDROUS EMOLLIENT GEL | | |
| Diethylhexyl naphthalate | emollient, refractive index increasing agent | 46 |
| Dow Corning 345 Fluid (Cyclomethicone) | emollient, skin conditioning agent | 25 |
| Laponite OP2 (LaPorte) | viscosity increasing agent | 20 |
| Ethanol SD 40 (anhyd.) | carrier, solvent | 9 |
| SUNTAN OIL | | |
| Dow Corning X2-1401 Fluid (dimethicone in cyclomethicone) | emollient, skin conditioning agent | 20 |
| Dow Corning 344 Fluid (cyclomethicone tetramer) | emollient, skin conditioning agent | 40 |
| Dow Corning 345 Fluid (cyclomethicone pentamer) | emollient, skin conditioning agent | 16 |
| Diisopropyl Adipate | emollient, skin conditioning agent | 10 |
| Diethylhexyl naphthalate | emollient, refractive index increasing agent | 10 |

-continued

|  | Function | % |
|---|---|---|
| Escalol 507 (Octyl Dimethyl PABA) | active sunscreen agent | 4 |
| CYCLOMETHICONE AFTER SHAVE | | |
| Alcohol SD 39C (anhyd.) | solvent, carrier | 35 |
| Diethylhexyl naphthalate | emollient, refractive index increasing agent | 50 |
| Panthenol (Roche) | emollient | 10 |
| Fragrance |  | 5 |

Manufacturing Procedure: Add the cyclomethicone last, slowly, following the premixing of the other ingredients. Let stand 72 hours before filtering.

As an example of a clear roll-on antiperspirant composition that has been actually reduced to practice, wherein the oil phase and the water phase have exactly the same refractive index, the following composition, having 2% by weight diethylhexyl naphthalate provides excellent clarity and emolliency.

CLEAR ROLL-ON ANTIPERSPIRANT

| | Chemical Name | Trade Name | Function | % w/w |
|---|---|---|---|---|
| Oil Phase (Refractive Index = 1.4078) A: | | | | |
| A. | Decamethylpentacyclomethicone | DC 345 (Dow Corning) | emollient, refractive index increasing agent | 11.00 |
| A. | Diethylhexyl naphthalate | HallBrite TQ (C. P. Hall) | emollient, refractive index increasing agent | 2.00 |
| A. | Dimethicone 100 cps | SF-96-100 (GE Silicones) | skin conditioning agent, emollient | 4.00 |
| A. | Dimethicone copolyol | DC 3225C (Dow Corning) | skin conditioning agent, emollient | 12.00 |
| Water Phase (Refractive Index = 1.407) B: | | | | |
| B. | Al Zr Tetrachlorhydrex-gly | 35B X3 43% aq (Westchlor) | active antiperspirant compound | 47.00 |
| B. | Methylpropylene glycol | MPDiol (Arco) | humectant | 13.50 |
| B. | Deionized water |  | carrier | 10.50 |

Procedure:
1. Combine "A" ingredients. Measure the refractive index of the oil phase.
2. Combine "B" ingredients. Measure the refractive index of the water phase.
3. Adjust the refractive index of the water phase by adding water (lower refractive index) or methylpropylene glycol (higher) to match refractive index of oil phase.
4. With low shear mixing, add a small portion of the water phase to the oil phase.
5. Gradually increase the shear, adding small portions of water phase until complete.

What is claimed is:

1. A composition, including a carrier selected from the group consisting of water, an organic compound, and mixtures thereof, the improvement comprising about 0.1% to about 20% by weight of a diester or polyester of a naphthalene dicarboxylic acid selected from the group consisting of formula (I), formula (II), formula (III) and mixtures thereof:

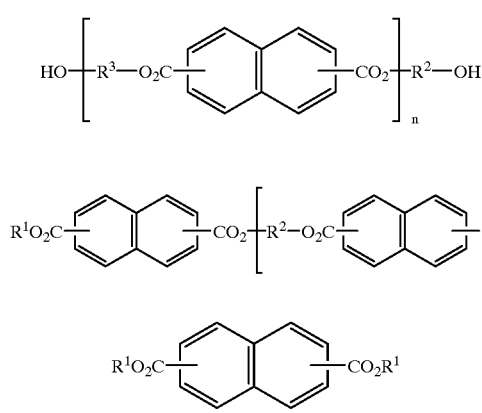

wherein each $R^1$, same or different, is selected from the group consisting of an alkyl group having 1 to 22 carbon atoms; a diol having the structure HO—$R^2$—OH; and a polyglycol having the structure HO—$R^3$—(—O—$R^2$—)$_m$—OH, wherein $R^2$ and $R^3$, same or different, are each an alkylene group, straight chain or branched, having 1 to 6 carbon atoms, and wherein m and n are each in the range of 1 to about 100, or a mixture thereof.

2. The composition of claim 1, including an oil phase and a water phase emulsified together to form a transparent oil and water emulsion.

3. A composition in accordance with claim 1, wherein the composition further includes a dibenzoylmethane derivative, and the molar ratio of said compound having formula (I), (II) or (III) to said dibenzoylmethane derivative is about 0.1:1 to about 10:1.

4. A composition in accordance with claim 1, wherein the molar ratio of said compound having formula (I), (II) or (III) to said dibenzoylmethane derivative is about 0.1:1 to about 0.3:1.

5. A composition in accordance with claim 4, wherein the dibenzoylmethane derivative is 4-(1,1-dimethylethyl)-4'-methoxydibenzoylmethane.

6. A composition in accordance with claim 5, wherein the dibenzoylmethane derivative is included in the composition in an amount of about 0.5% to about 5% by weight of the composition.

7. A composition in accordance with claim 1, wherein the polyester is a polyester of 2,6-naphthalene dicarboxylic acid.

8. The composition of claim 2, wherein the cosmetically acceptable carrier comprises a silicone fluid in an amount of about 1% to about 20% by weight of the composition.

9. A method of applying a cosmetic composition onto human skin comprising topically applying to said skin a composition, in a cosmetically acceptable carrier, a diester or polyester of a naphthalene dicarboxylic acid compound selected from the group consisting of formula (I), formula (II), formula (III) and mixtures thereof:

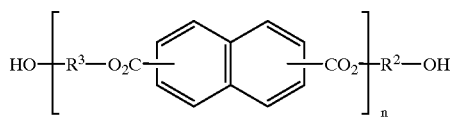

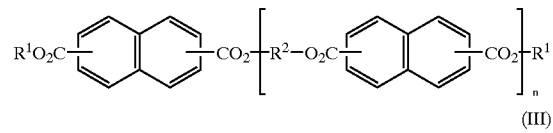

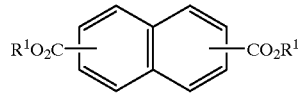

wherein each $R^1$, same or different, is selected from the group consisting of an alkyl group having 1 to 22 carbon atoms; a diol having the structure HO—$R^2$—OH; and a polyglycol having the structure HO—$R^3$—(—O—$R^2$—)$_m$—OH, wherein $R^2$ and $R^3$, same or different, are each an alkylene group, straight chain or branched, having 1 to 6 carbon atoms, and wherein m and n are each in the range of 1 to about 100, or a mixture thereof.

10. The method of claim 9, wherein the cosmetic composition includes an active antiperspirant compound in an effective amount.

11. The method of claim 10, wherein the antiperspirant compound is aluminum chlorhydrate.

12. The method of claim 9, wherein the composition includes an emollient in an amount of about 1% to about 50% of the composition.

13. A method of applying a transparent cosmetic formulation to human skin comprising topically applying to said skin, in a cosmetically acceptable carrier, a diester or polyester of a naphthalene dicarboxylic acid compound selected from the group consisting of formula (I), formula (II), formula (III) and mixtures thereof:

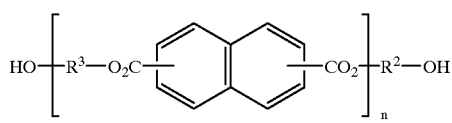

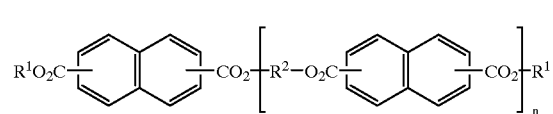

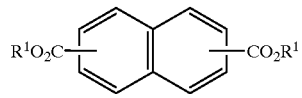

wherein each $R^1$, same or different, is selected from the group consisting of an alkyl group having 1 to 22 carbon atoms; a diol having the structure HO—$R^2$—OH; and a polyglycol having the structure HO—$R^3$—(—O—$R^2$—)$_m$—OH, wherein $R^2$ and $R^3$, same or different, are each an alkylene group, straight chain or branched, having 1 to 6 carbon atoms, and wherein m and n are each in the range of 1 to about 100, or a mixture thereof.

14. The method of claim 13, wherein the cosmetically acceptable carrier comprises a silicone fluid in an amount of about 1% to about 20% by weight of the composition.

15. The method of claim 13, wherein the cosmetic composition include an active antiperspirant compound in an effective amount.

16. The method of claim 15, wherein the antiperspirant compound is aluminum chlorhydrate.

17. The method of claim 13, wherein the composition includes an emollient in an amount of about 1% to about 50% of the composition.

* * * * *